US00PP27598P2

(12) United States Plant Patent
Kolk

(10) Patent No.: US PP27,598 P2
(45) Date of Patent: Jan. 24, 2017

(54) ***HYDRANGEA* PLANT NAMED 'KLAHYFLA'**

(50) Latin Name: *Hydrangea macrophylla*
Varietal Denomination: KLAHYFLA

(71) Applicant: Jacobus Wilhelmus Petrus Kolk, Amstelveen (NL)

(72) Inventor: Jacobus Wilhelmus Petrus Kolk, Amstelveen (NL)

( * ) Notice: Subject to any disclaimer, the term of this patent is extended or adjusted under 35 U.S.C. 154(b) by 68 days.

(21) Appl. No.: 14/544,822

(22) Filed: Feb. 23, 2015

(51) Int. Cl.
*A01H 5/00* (2006.01)

(52) U.S. Cl.
USPC ..... Plt./250

(58) Field of Classification Search
USPC ..... Plt./226, 250
See application file for complete search history.

(56) References Cited

PUBLICATIONS

Concept Plants website. https://conceptplants.com/varieties/hydrangea-macrophylla-onyx-flamingo/. Accessed Jun. 16, 2016. 2 pages.*
Rhododendron-Loder plants website.http://www.rhododendrons.com/hydrangeas/product/10676/1. Accessed Jun. 16, 2016. 1 page.*
Plantentiun Esveld website. http://www.esveld.nl/htmldiaen/h/hymfla.htm. Accessed Jun. 16, 2016. 2 pages.*
Future Gardens website. http://www.futuregardens.pl/hortensja-ogrodowa-zebra-hydrangea-macrophylla-black-steel-white-duplikat-1.html. Accessed Jun. 16, 2016. 6 pages.*
PLUTO: Plant variety Database, Jun. 11, 2016, citation for 'Flamingo'.*
Van Klaveren Plant website. http://www.vanklaverenplant.nl?p=hortensia&hcat=pothortensia%27s&categorie=74&product=174&lang=_en. Accessed Jun. 16, 2016. 1 page.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hydrangea macrophylla* named 'KLAHYFLA' that is characterized by its inflorescence with sepals of the sterile flowers that open light pink with a light greenish white base and mature to light purple-pink, its sturdy stems that are dark purple-brown (near black) in color, and its free flowering habit with sturdy inflorescences.

3 Drawing Sheets

Genus/species: *Hydrangea macrophylla.*
Varietal denomination: 'KLAHYFLA'.

BACKGROUND OF THE INVENTION

The present invention relates to a new and distinct cultivar of *Hydrangea macrophylla* and will be referred to hereafter by its cultivar name, 'KLAHYFLA'. 'KLAHYFLA' represents a new bigleaf *hydrangea*, a perennial shrub grown for landscape use.

The Inventor discovered the new cultivar in 2006 as a naturally occurring branch mutation of *Hydrangea* 'Verena' (not patented) that was growing in a container located in a greenhouse in Amstelveen, The Netherlands.

Asexual propagation of the new cultivar was first accomplished by softwood stem cuttings by the Inventor in Amstelveen, The Netherlands in 2010. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'KLAHYFLA' as a unique cultivar of *Hydrangea macrophylla.*

1. 'KLAHYFLA' exhibits inflorescence with sepals of the sterile flowers that open light pink with a fight greenish white base and mature to light purple-pink.

2. 'KLAHYFLA' exhibits sturdy sterns that are dark purple-brown (near black) in color.
3. 'KLAHYFLA' is free flowering with sturdy inflorescences.

The parent plant of 'KLAHYFLA', 'Verena', differs from 'KLAHYFLA' in having inflorescences that are mauve pink in color. 'KLAHYFLA' can be most closely compared to the cultivar 'Zebra' (U.S. Plant Pat. No. 18,688) and 'Nigra' (not patented). Both are similar to 'KLAHYFLA' in having nearly black colored stems. 'Zebra' differs from 'KLAHYFLA' in having sterile flowers that are white in color. 'Nigra' differs from 'KLAHYFLA' in having smaller and less sturdy inflorescences, in having thinner and less sturdy stems, and in having a larger plant size.

BRIEF DESCRIPTION OF THE DRAWINGS

The photographs in the figures were taken of a two year-old plant of 'KLAHYFLA' as grown in an unheated greenhouse in a 22-cm container in Amstelveen, The Netherlands.

The photograph in FIG. 1 illustrates a side view of 'KLAHYFLA' in bloom.

Figure 1:
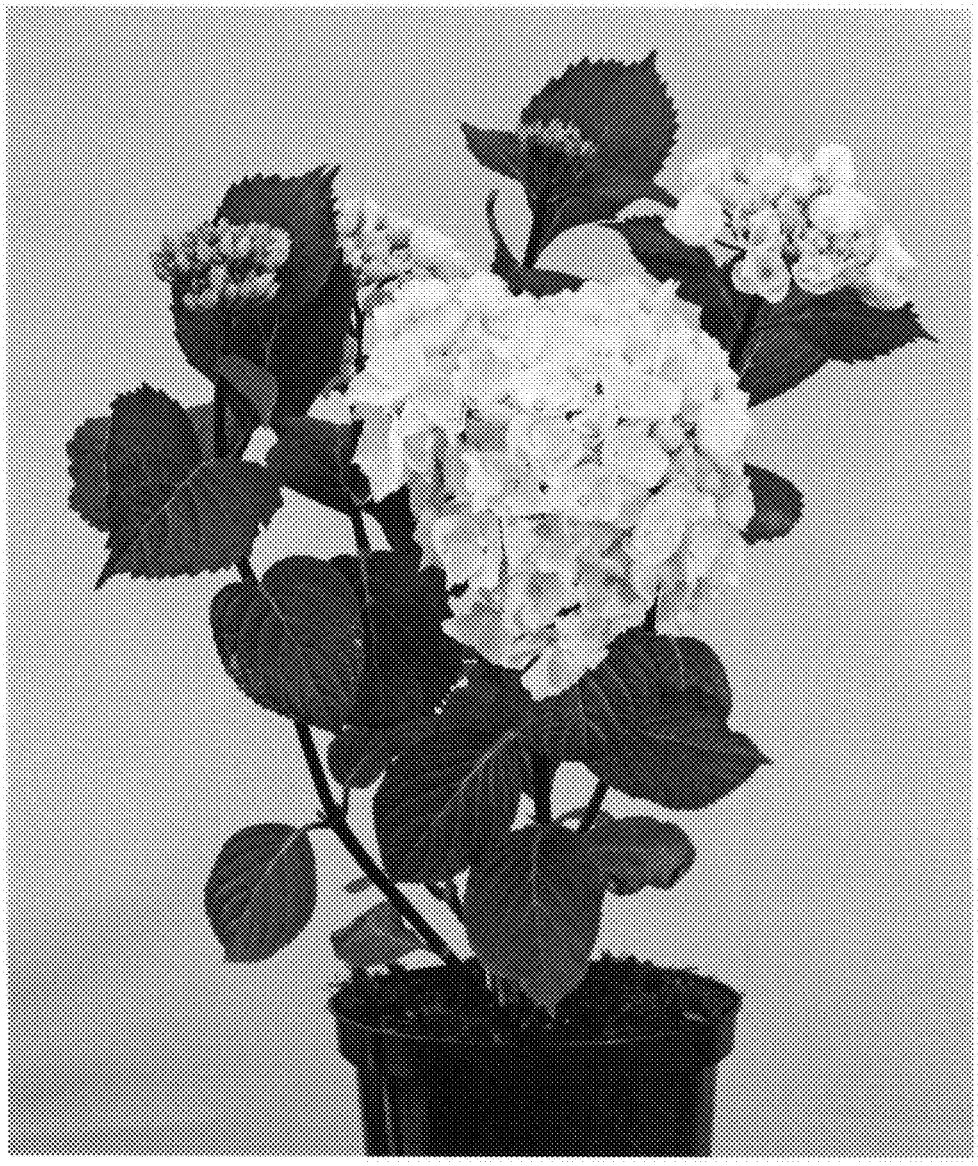
Figure 2:
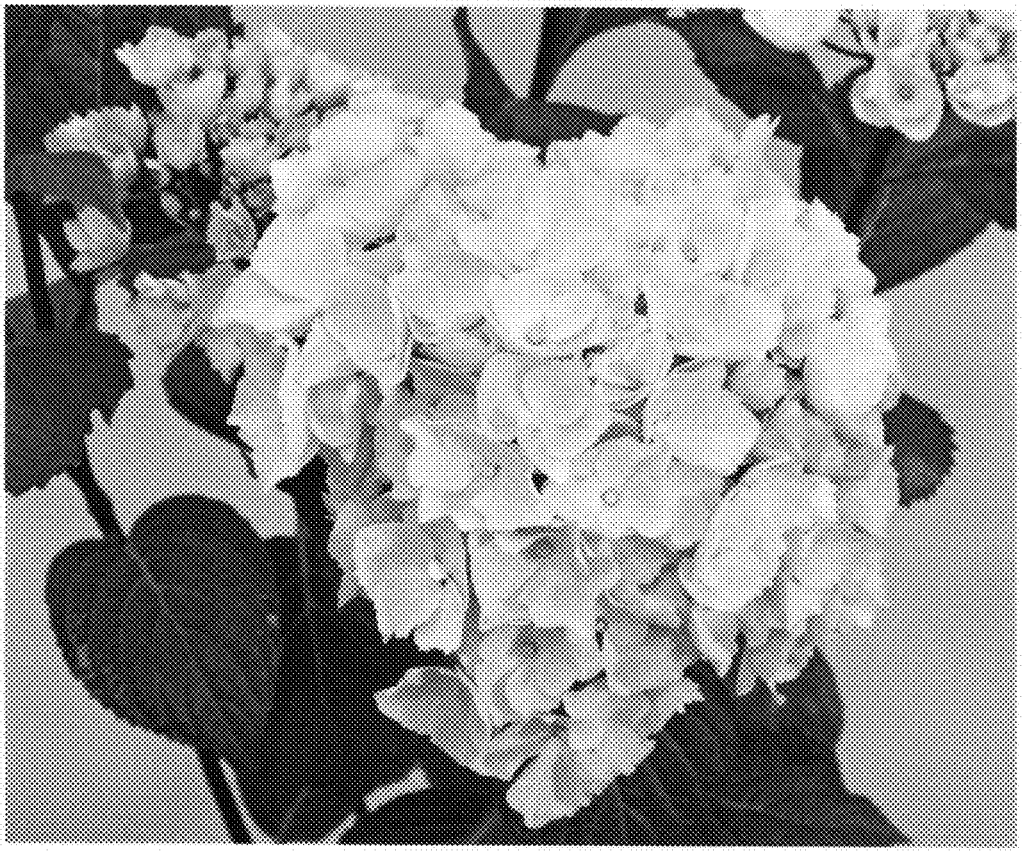

The photograph in FIG. 2 provides a close-up view of an inflorescence of 'KLAHYFLA'.

Figure 3:
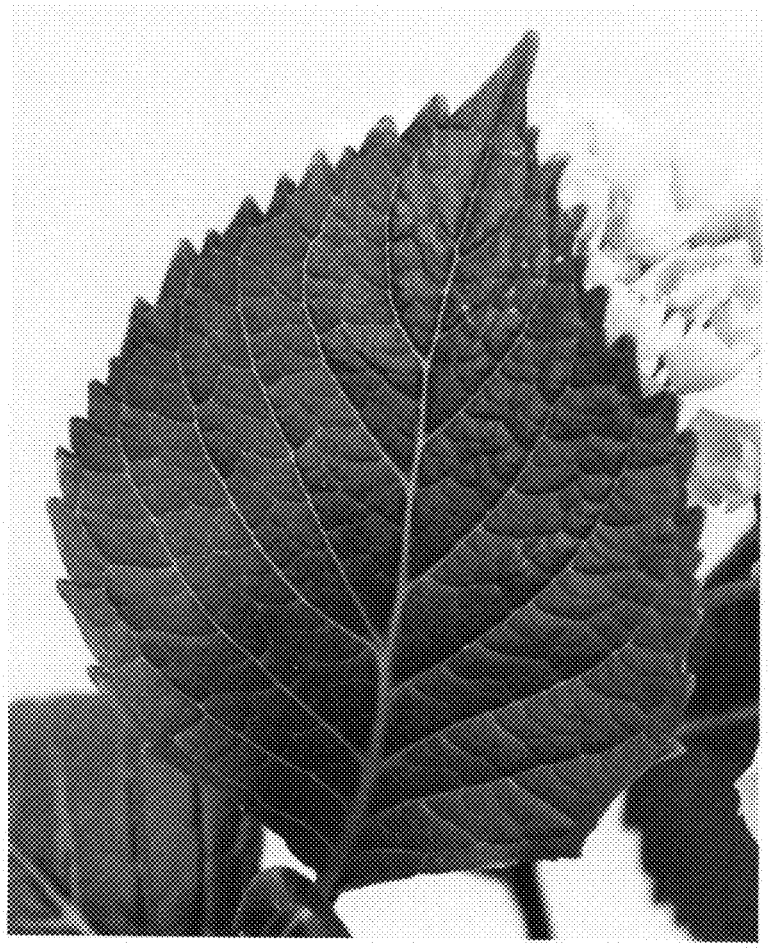

The photograph in FIG. 3 provides a close-up view of a leaf of 'KLAHYFLA'.

Figure 4:
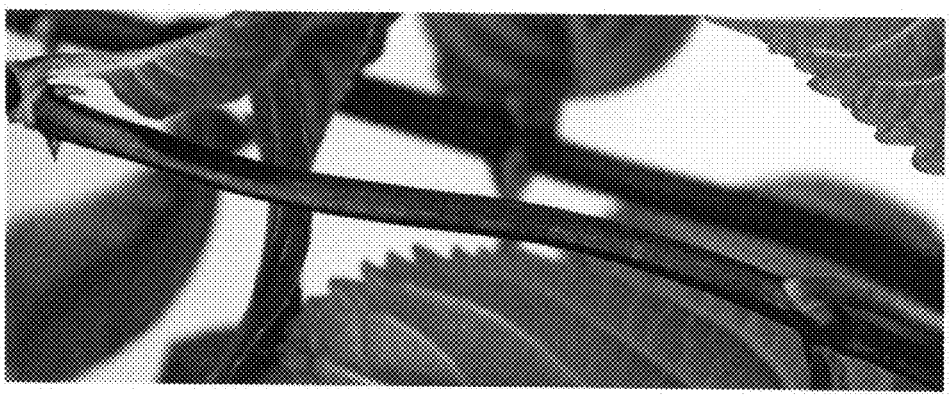

The photograph in FIG. 4 provides a close-up view of a stem of 'KLAHYFLA'.

The colors in the photographs are as close as possible with the digital photography and printing techniques utilized mid the color codes in the detailed botanical description accurately describe the new *Hydrangea*.

BOTANICAL DESCRIPTION OF THE PLANT

The following is a detailed description of two year-old plants as grown under greenhouse conditions in 22-cm containers in a greenhouse in June in Amstelveen, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late spring to late summer in The Netherlands.

*Plant type*.—Deciduous shrub.

*Plant habit*.—Broadly upright, sturdy stems.

*Height and spread*.—Average 52 cm in height and 44.3 cm in diameter for a two year-old plant as grown in a 22-cm container.

*Hardiness*.—At least in U.S.D.A. Zones 5 to 9.

*Diseases and pests*.—No susceptibility or resistance to pests and diseases has been observed.

*Root description*.—Fibrous, dense, moderately branched and primarily 159A in color.

*Propagation*.—Softwood stem cuttings.

*Root development*.—Roots initiate in 4 to 5 weeks and fully develop as a young rooted plant in 3 months (average day temperatures of 20° C.).

*Growth rate and vigor*.—Moderate.

Stem description:

*Stem shape*.—Round.

*Stem strength*.—Strong.

*Stem aspect*.—Upright to an average angle of 70°.

*Stem color*.—Immature stem; between N186C and 200A, mature stem; a blend of 199A, 199B and N199D.

*Stem size*.—Average of 40.5 cm in length (excluding the inflorescence) and 7 mm in diameter.

*Stem surface*.—Glabrous.

*Branching*.—Moderately, freely branching, with an average of 4 lateral branches.

*Internode length*.—Average of 9.9 cm.

Foliage description:

*Leaf shape*.—Broad elliptic to broad ovate.

*Leaf arrangement*.—Opposite.

*Leaf division*.—Simple.

*Leaf number*.—Average of 8 (4 pairs) per lateral branch.

*Leaf base*.—Obtuse to short attenuate.

*Leaf apex*.—Broad apiculate.

*Leaf margins*.—Serrated.

*Leaf venation*.—Pinnate, upper surface; 144C, lower surface; 146C to 146D.

*Leaf size*.—Average of 12.5 cm in length and 9.2 cm in width.

*Leaf attachment*.—Petiolate.

*Leaf surface*.—Upper and lower surface; smooth and moderately rugose.

*Leaf color*.—Immature upper surface; between 143C and 144A, immature lower surface; 144A to 144B, mature upper surface; N137A, mature lower surface; 147B.

*Petioles*.—Average of 1.9 cm in length and 3.5 mm in diameter, upper surface color; 144C, tinged 199B, lower surface color; 199B, upper and lower surfaces are smooth and very slightly glossy.

Inflorescence description:

*Inflorescence type*.—Flattened globular, mophead form, compound corymb of single sterile and fertile flowers.

*Lastingness of inflorescence*.—Sterile flowers; persistent, lasting about 6 weeks, fertile flowers; self-cleaning, lasting about 1 week.

*Inflorescence number*.—One per lateral or sublateral stem.

*Inflorescence size*.—Average of 14 cm in height and 19.7 cm in diameter.

*Flower number*.—An average of 165 sterile flowers and 70 fertile flowers per inflorescence.

*Flower fragrance*.—None.

*Flower aspect*.—Sterile flowers; upright to outward and slightly drooping, fertile flowers; upright.

*Flower size*.—Sterile flowers; rotate in shape, average of 5.2 cm in diameter and 1.5 cm in depth, fertile flowers; rotate, petals are dropped when maturing, average of 7 mm in diameter and 5 mm in depth.

*Flower buds*.—Sterile flowers; average of 7 mm in length and 4 mm in diameter, ovate in shape and 145A in color, fertile flowers; average of 5 mm in length and 4 mm in diameter, broad ovate in shape, 150D in color with base 144A.

*Peduncles*.—Average of 6 cm in length and 4.5 mm in width, held upright, strong, 53B in color, surface is moderately covered with thin pubescent hairs, average of 0.2 mm in length too small to be measured by RHS-CC.

*Pedicels*.—Sterile Flowers; average of 3.4 cm in length and 2 mm in diameter, held at an average angle of 30°, strong, 53B in color, surface is moderately covered with thin pubescent hairs, average of 0.2 mm in length and too small to be measured by RHS-CC, fertile flowers; average of 6 mm in length and 1 mm in diameter, at an average angle of 15°, moderate in strength, N199B to N199D in color, surfaces are matte and smooth.

*Petals*.—Sterile flowers; average of 5 in a rotate arrangement, ovate to concave in shape, acute apex, cuneate base, entire margin, average of 4 mm in length and 2 mm in width, upper and lower surfaces glabrous, color: upper surface when opening and fully open; NN155C to NN155D, lower surface when opening and fully open; N155B, not fading, but dropped when mature, fertile flowers; average of 5 in a rotate arrangement, ovate and concave in shape, acute apex, cuneate base, entire margin, average of 3 mm in length and 1.5 mm in width, upper and lower surface texture is glabrous and matter, color: upper and lower surface when opening; 150D, fading color of upper and lower surface; 76B, tips are 150D, upper and lower surface when fully opened; petals drop when mature.

*Sepals*.—Sterile flowers; average of 4, rotate in arrangement, slightly overlapping, both surfaces smooth and matte, broad rhomboidal to deltoid in shape, margin is dentate, bluntly obtuse apex, broad acuminate base, an average of 2.5 cm in length and 3 cm in width, color: upper surface when opening; 62D, base a blend of 155A to 150D, lower surface when opening; 73D, base 150D, upper surface when fully open; 73B to 73C, lower surface when fully open; 73D to 73C, fading to upper side; 75D with tips 144B, fading to lower side; 76D with tips 144B, fertile flowers; average of 5, rotate in arrangement, both surfaces glabrous and matte, ovate in shape, margin is entire, acute apex, broad cuneate base, an average of 1.5 mm in length and 0.15 mm in width, color: upper and lower surface when opening; 144A, upper and lower surface when fully open; 145A to 150B.

Reproductive organs:

*Androecium*.—Sterile flowers; average of 10 stamens, filaments are 3 mm in length and NN155DA in color, anther is broadly kidney-shaped, 0.5 mm in length and 155B in color, pollen is low to moderate in quantity and 155A in color, fertile flowers; average of 10 stamens, filaments are 2.5 mm in length and NN155D in color, anthers are broad kidney-shaped, 0.5 mm in length and 155B in color, pollen is moderate in quantity and 155A in color.

*Gynoecium*.—Sterile flowers; average of 3 pistils, 1 mm in length, stigma is club-shaped and NN155C to NN155D in color, style is 0.5 mm in length and 157D in color, ovary is 157D in color, fertile flowers; average of 3 pistils, 1.5 mm in length, stigma is club-shaped and NN155C to NN155D in color, style is 1 mm in length and 157D in color, ovary is 157C in color.

*Fruit and seed*.—No seeds or fruit observed to date.

It is claimed:

1. A new and distinct cultivar of *Hydrangea* plant named 'KLAHYFLA' substantially as herein illustrated and described.

* * * * *